United States Patent [19]

Howard

[11] Patent Number: 5,917,089
[45] Date of Patent: Jun. 29, 1999

[54] PROCESS FOR THE CARBONYLATION OF AN ALCOHOL AND/OR A REACTIVE DERIVATIVE THEREOF

[75] Inventor: Mark Julian Howard, North Humberside, United Kingdom

[73] Assignee: BP Chemicals Limited, London, United Kingdom

[21] Appl. No.: 08/694,556

[22] Filed: Aug. 9, 1996

[30] Foreign Application Priority Data

Aug. 22, 1995 [GB] United Kingdom ............ 9517184

[51] Int. Cl.⁶ .......................... C07C 51/12; C07C 69/00
[52] U.S. Cl. ................................. 562/519; 560/129
[58] Field of Search ............................ 560/129; 562/519

[56] References Cited

U.S. PATENT DOCUMENTS

| | | | |
|---|---|---|---|
| 2,743,296 | 4/1956 | Painter et al. | 260/547 |
| 5,189,203 | 2/1993 | Hansen et al. | 560/232 |
| 5,510,523 | 4/1996 | Yamaseki et al. | 562/519 |
| 5,510,524 | 4/1996 | Garland et al. | 562/519 |

FOREIGN PATENT DOCUMENTS 685446  12/1995  European Pat. Off. .

*Primary Examiner*—José G. Dees
*Assistant Examiner*—Barbara Badio
*Attorney, Agent, or Firm*—Fay, Sharpe, Beall, Fagan, Minnich & McKee

[57] ABSTRACT

A carbonylation process which comprises (a) contacting, in a first carbonylation reactor at elevated temperature and pressure, an alcohol having n carbon atoms and/or a reactive derivative thereof with carbon monoxide in a liquid reaction composition comprising a halogen and/or halogen compound promoter and a Group VIII noble metal carbonylation catalyst to produce a carbonylation product comprising a carboxylic acid having n+1 carbon atoms and/or an ester of the carboxylic acid having n+1 carbon atoms and the alcohol having n carbon atoms and/or any anhydride of the carboxylic acid having n+1 carbon atoms, (b) withdrawing from the first carbonylation reactor, an off-gas stream comprising carbon monoxide and optionally halogen and/or halogen compound promoter, and optionally carbonylation production; and (c) contacting in a second carbonylation reactor, the withdrawn off-gas stream with an alcohol having m carbon atoms and/or reactive derivative thereof in the presence of a halogen and/or halogen compound promoter and a heterogenous carbonylation catalyst comprising a supported Group VIII noble metal to produce a further carbonylation product comprising a carboxylic acid having m+1 carbon atoms and/or an ester of the carboxylic acid having m+1 carbon atoms and the alcohol having m carbon atoms and/or an anhydride of the carboxylic acid having m+1 carbon atoms.

26 Claims, 1 Drawing Sheet

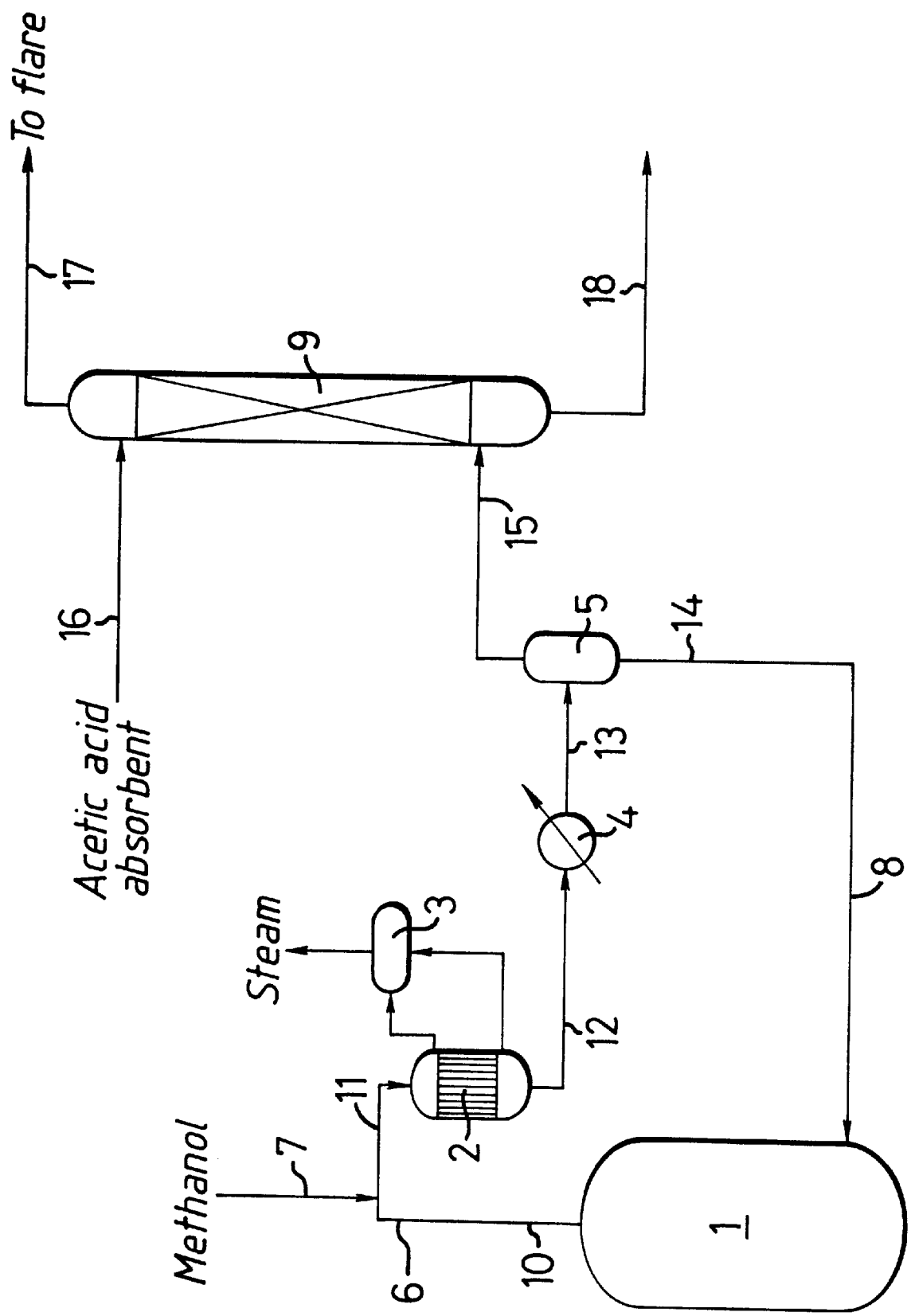

PROCESS FOR THE CARBONYLATION OF AN ALCOHOL AND/OR A REACTIVE DERIVATIVE THEREOF

The present invention relates to a process for the carbonylation of an alcohol and/or a reactive derivative thereof.

The production of acetic acid by rhodium-catalysed, iodide-promoted carbonylation of methanol in a homogeneous liquid-phase reaction medium is a known process and is operated on a commercial scale. Although such a process is highly selective, there is a gradual build-up in the carbonylation reactor of inert gaseous impurities such as nitrogen from the carbon monoxide feed gas and of by-product gases such as, methane, hydrogen and carbon dioxide. The build-up of these gases in the reactor is controlled by venting off-gas from the reactor to keep the standing concentration of these undesirable gases in the reactor to an acceptable level. The vented off-gas contains carbon monoxide in addition to the undesirable inert and by-product gases. The vented off-gas may additionally comprise volatile iodide compound promoter, acetic acid product, water and unreacted methanol and/or methyl acetate reactant. Similar venting of off-gas is known in carbonylation processes for the production of acetic anhydride by carbonylation of methyl acetate, in which case the off-gas is essentially free of water vapour.

In known processes, off-gas vented from a carbonylation reactor is processed through a recovery unit, such as a scrubber system, in which volatile halogen and/or halogen compound promoters and carboxylic acid are recovered and ultimately returned to the carbonylation reactor. The remaining gas, which comprises carbon monoxide and the undesirable inert and by-product gases, is then usually burned. Scrubbing systems for off-gases vented from carbonylation reactors are described for example in JP 61058803, AU 8288598 and U.S. Pat. No. 4,241,219.

A disadvantage of such scrubbing/burning systems is that the burnt carbon monoxide represents a loss of the overall conversion of carbon monoxide to carbonylation products in the plant. This is particularly a disadvantage when the source of carbon monoxide limits the overall plant productivity.

It has now been found that the off-gas vented from a liquid-phase carbonylation process can be used as a feed gas to a second carbonylation reactor in which the carbon monoxide in the off-gas is converted to carbonylation product.

Thus, according to one aspect of the present invention there is provided a carbonylation process which comprises (a) contacting, in a first carbonylation reactor at elevated temperature and pressure, an alcohol having n carbon atoms and/or a reactive derivative thereof with carbon monoxide in a liquid reaction composition comprising a halogen and/or halogen compound promoter and a Group VIII noble metal carbonylation catalyst to produce a carbonylation product comprising a carboxylic acid having n+1 carbon atoms and/or an ester of the carboxylic acid having n+1 carbon atoms and the alcohol having n carbon atoms and/or an anhydride of the carboxylic acid having n+1 carbon atoms; (b) withdrawing from the first carbonylation reactor, an off-gas stream comprising carbon monoxide and optionally halogen and/or halogen compound promoter, and optionally carbonylation product; and (c) contacting in a second carbonylation reactor, the withdrawn off-gas stream with an alcohol having m carbon atoms and/or a reactive derivative thereof in the presence of a halogen and/or halogen compound promoter and a heterogeneous carbonylation catalyst comprising a supported Group VIII noble metal to produce a further carbonylation product comprising a carboxylic acid having m+1 carbon atoms and/or an ester of the carboxylic acid having m+1 carbon atoms and the alcohol having m carbon atoms and/or an anhydride of the carboxylic acid having m+1 carbon atoms.

The process of the present invention overcomes the disadvantage of the prior art by converting carbon monoxide in the off-gas vented from the first carbonylation reactor to carbonylation product in the second carbonylation reactor thereby increasing the overall yield of carbonylation products from carbon monoxide in the carbonylation plant. This is particularly beneficial when the source of carbon monoxide is limiting the capacity of the plant.

The process of the present invention will reduce or even eliminate completely the amount of carbon monoxide in the vented off-gas which is burned from a liquid-phase carbonylation process.

Another advantage of the process of the present invention is that the off-gas from the first carbonylation reactor can be used in the second carbonylation reactor without purification.

Yet a further advantage of the process of the present invention is that the off-gas from the first carbonylation reactor may be optionally used without cooling.

In the first and second carbonylation reactors, the alcohol reactants may independently be an aliphatic alcohol having up to 12 carbon atoms, preferably up to 6 carbon atoms including methanol, ethanol, propanol and isopropanol, butanols, pentanols and hexanols. A preferred alcohol is methanol, the carbonylation product of which is acetic acid and/or methyl acetate. Reactive derivatives of the alcohol include dialkyl ethers having alkyl moieties each having n or m carbon atoms as the case may be, alkyl halides, preferably iodides, having n or m carbon atoms as the case may be and esters of alcohols having n or m carbon atoms with carboxylic acids having n+1 or m+1 carbon atoms as the case may be, wherein n and m are independently suitably up to 12, preferably up to 6. Suitable reactive derivatives of methanol include methyl acetate, dimethyl ether and methyl iodide. A mixture of more than one alcohol may be used in either reactor. A mixture of alcohol and reactive derivatives thereof may be used in either reactor. Preferably, methanol and/or methyl acetate are used as reactants in the reactors. Preferably, the number of carbon atoms, m, of the alcohol in the second carbonylation reactor is the same as the number of carbon atoms, n, of the alcohol of the first carbonylation reactor, but the reactants need not be the same. Thus, for example, methanol may be used as reactant in the first reactor, but methanol and/or a reactive derivative thereof may be used as reactant in the second reactor.

In the first and second carbonylation reactors, as promoter there may be used either a halogen or a halogen compound, which may be for example hydrogen halide, an alkyl or aryl halide, a metal halide or an ammonium, phosphonium, arsonium or stibonium halide. Promoters containing iodine as the halogen moiety are preferred. Preferably, the promoter is an alkyl iodide, preferably having an alkyl moiety corresponding to the alcohol reactant and/or its reactive derivative, for example methyl iodide.

The First Carbonylation Reactor

The homogenous liquid-phase carbonylation process in the first carbonylation reactor may be any suitable process for the carbonylation of an alcohol having n carbon atoms and/or reactive derivative thereof to produce a carbonylation product comprising a carboxylic acid having n+1 carbon atoms and/or an ester of the carboxylic acid having n+1 carbon atoms and the alcohol having n carbon atoms and/or an anhydride of the carboxylic acid having n+1 carbon atoms.

Thus acetic acid and its corresponding anhydride may be manufactured by carbonylation of methanol as described for example in GB-A-1233121 and GB-A-1234641 and the production of acetic anhydride with or without the net coproduction of acetic acid from methanol and carbon monoxide in a series of esterification, carbonylation and separation steps is described in EP-A-0087870.

The Group VIII noble metal catalyst in the liquid carbonylation reaction composition in the first carbonylation reactor is preferably an iridium or rhodium-containing compound which is soluble in the liquid reaction composition. The iridium or rhodium catalyst may be added to the liquid reaction composition for the carbonylation reaction in any suitable form which dissolves in the liquid reaction composition or is convertible to a soluble form.

Examples of suitable iridium-containing compounds which may be added to the liquid reaction composition in the first carbonylation reactor include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-$, $[Ir(CO)_2Br_2]^-$, $[Ir(CO)_2I_2]^-$, $[Ir(CH_3)I_3(CO)_2]^-$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$, preferably, chloride-free complexes of iridium such as acetates, oxalates and acetoacetates.

Preferably, the concentration of iridium catalyst in the liquid reaction composition in the first carbonylation reactor is in the range 100 to 6000 ppm by weight of iridium.

Examples of suitable rhodium-containing compounds which may be added to the liquid reaction composition in the first carbonylation reactor include $[Rh(CO)_2Cl]_2$, $[Rh(CO)_2I]_2$, $[Rh(Cod)Cl]_2$, rhodium (III) chloride, rhodium (III) chloride trihydrate, rhodium (III) bromide, rhodium (III) iodide, rhodium (III) acetate, rhodium dicarbonylacetylacetonate, $RhCl_3(PPh_3)_3$ and $RhCl(CO)(PPh_3)_2$.

Preferably, the concentration-of the rhodium catalyst in the liquid reaction composition in the first carbonylation reactor is in the range from 1 ppm up to its limit of solubility in the reactor and/or product recovery system, typically 10 to 1500 ppm by weight of rhodium.

When the Group VIII noble metal catalyst in the liquid reaction composition in the first carbonylation reactor is iridium, the liquid reaction composition may contain an optional co-promoter selected from the group consisting of ruthenium, osmium, rhenium, cadmium, mercury, zinc, indium and gallium.

When the Group VIII noble metal in the liquid reaction composition in the first carbonylation reactor is rhodium, the liquid reaction composition may contain an optional co-promoter selected from alkali metals and/or an organic iodide, such as a quaternary ammonium iodide.

At least some of the alcohol and/or reactive derivative thereof will be converted to, and hence present as ester of the alcohol with the carboxylic acid product in the liquid reaction composition by reaction with carboxylic acid product or solvent. For example, methanol will be present as methyl acetate. The concentration of ester in the liquid reaction composition for rhodium-catalysed carbonylations is suitably in the range 0.1 to 70% by weight, preferably 0.5 to 50% by weight, more preferably 0.5 to 35% by weight and for iridium-catalysed carbonylations is preferably 1 to 70%, more preferably 2 to 50% and yet more preferably 3 to 35% by weight.

Water may be formed in situ in the liquid reaction composition in the first carbonylation reactor, for example, by the esterification reaction between alcohol reactant and carboxylic acid product. Water may be introduced to the carbonylation reactor together with or separately from other components of the liquid reaction composition. Water may be separated from other components of the reaction composition withdrawn from the reactor and may be recycled in controlled amounts to maintain the required concentration of water in the liquid reaction composition. Preferably, the concentration of water in the liquid reaction composition is in the range 0.1 to 15% by weight, more preferably 1 to 15% by weight, most preferably 1 to 10% by weight in processes for producing carboxylic acids. Alternatively, the process may be substantially anhydrous, for example less than 0.1% water by weight, where the carboxylic acid anhydride is a desired product.

The concentration of the halogen or a halogen compound promoter used in the liquid reaction composition in the first carbonylation reactor is preferably in the range 1 to 20% by weight, more preferably 2 to 15% by weight.

A solvent, preferably the carboxylic acid and/or ester product may be used in the first carbonylation reactor.

The carbon monoxide reactant in the first carbonylation reactor may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction in the first carbonylation reactor is preferably kept low, for example, less than 1 bar partial pressure, as its presence may result in the formation of hydrogenation products. The partial pressure of carbon monoxide in the first carbonylation reactor is suitably in the range 1 to 70 bar, preferably 1 to 35 bar, and most preferably 1 to 15 bar.

The pressure of the carbonylation reaction in the first carbonylation reactor is suitably in the range 10 to 200 barg, preferably 10 to 100 barg, most preferably 15 to 50 barg. The temperature of the carbonylation reaction in the first carbonylation reactor is suitably in the range 100 to 300° C., preferably in the range 150 to 220° C.

The liquid phase carbonylation process in the first carbonylation reactor may be operated as either a batch or continuous, preferably a continuous process.

Carboxylic acid and/or ester and/or acid anhydride product from the first carbonylation reactor may be recovered by withdrawing liquid reaction composition from the reactor and separating the carboxylic acid and/or ester and/or acid anhydride product in one or more flash and/or distillation stages from other components such as the Group VIII metal catalyst, halogen or halogen compound promoter, water and unconsumed reactants which may be recycled to maintain their concentrations in the first carbonylation reactor.

The Second Carbonylation Reactor

Off-gas withdrawn from the first carbonylation reactor comprising carbon monoxide is contacted in a second carbonylation reactor with an alcohol having m carbon atoms and/or a reactive derivative thereof in the presence of a halogen and/or halogen compound promoter and a heterogeneous carbonylation catalyst comprising a supported Group VIII noble metal to produce a carbonylation product comprising carboxylic acid having m+1 carbon atoms and/or an ester of the carboxylic acid having m+1 carbon atoms and the alcohol having m carbon atoms and/or an anhydride of the carboxylic acid having m+1 carbon atoms.

In the heterogeneous carbonylation process in the second carbonylation reactor, the alcohol and/or reactive derivative thereof may be in the liquid and/or vapour phase.

The alcohol and/or reactive derivative thereof used in the second carbonylation reactor may be introduced to the second carbonylation reactor together with and/or separately from the off-gas from the first carbonylation reactor. The off-gas withdrawn from the first carbonylation reactor may additionally comprise alcohol and/or reactive derivative thereof. The alcohol and/or reactive derivative thereof may be introduced to the second carbonylation reactor by mixing with hot vented off-gas from the first carbonylation reactor either as a liquid at ambient temperature or as a vapour at elevated temperature, thereby introducing a gas, vapour and/or liquid mixture into the second carbonylation reactor. A suitable liquid injector may be required to reduce thermal shock of the mixing process. It is expected that injection of liquid alcohol and/or reactive derivative thereof into the hot vented off-gas will cause some condensation of vapours in the vented off-gas. Previous heating and vaporisation of the alcohol and/or reactive derivative thereof may be employed in order to avoid condensation in the total feed to the second carbonylation reactor. Suitably, the off-gas vented from the first carbonylation reactor will be at the elevated temperature and pressure of the first carbonylation reactor, for example at a temperature in the range 100 to 300° C., preferably in the range 150 to 220° C., for example about 188° C., and at a pressure in the range 10 to 200 barg, preferably 10 to 100 barg, most preferably 15 to 50 barg, for example about 28.6 barg.

Optionally, the off-gas withdrawn from the first carbonylation reactor may be passed through a condenser and knock-out pot to remove some of the condensable components before being admitted to the second carbonylation reactor.

Preferably, the off-gas withdrawn from the first carbonylation reactor additionally comprises volatile halogen and/or halogen compound promoter. This may be sufficient for the requirements of the second carbonylation reactor, or additional halogen and/or halogen compound promoter may be introduced to the second carbonylation together with and/or separately from the off-gas.

The off-gas withdrawn from the first carbonylation reactor may additionally comprise carboxylic acid and/or ester product.

The liquid Hourly Space Velocity for continuous operation of the second carbonylation reactor may be in the range 0.05 to 10 and the feed gas to the feed liquid ratio may suitably be in the range 0.1:1 to 10:1, though higher or lower ratios may be employed.

The second carbonylation reactor may be a multi-tubed heterogeneous reactor packed with a suitable heterogeneous carbonylation catalyst.

Any suitably active heterogeneous carbonylation catalyst may be used in the second carbonylation reactor. Preferably, the heterogeneous carbonylation catalyst in the second carbonylation reactor comprises a Group VIII metal selected from the group consisting of iridium, rhodium and nickel, and an optional metal promoter, on an inert support.

Preferably, the heterogeneous catalyst in the second carbonylation reactor may suitably comprise from 0.1 to 20% by weight Group VIII metal and optionally from 0.1 to 20% by weight of metal promoter.

If a metal promoter is present in the catalyst composition, the weight ratio Group VIII metal:metal promoter may suitably be in the range 200:1 to 1:200.

Suitable metal promoters include iron, nickel, lithium and cobalt.

Preferably the inert support is carbon. The carbon support may be any suitable activated or inactivated high surface area carbon or high surface area graphite. Preferred supports are the high surface area activated carbons. Examples of such materials are high surface area carbons having a surface area in excess of 500 $m^2g^{-1}$. Suitably macroporous, mesoporous or microporous carbon may be used.

Preferably, the heterogeneous catalyst for use in the second carbonylation reactor comprises rhodium and optionally ruthenium supported on a carbon support. Alternatively, iridium with optional ruthenium may be used on a carbon support.

The catalyst for use in the second carbonylation reactor may be prepared by impregnating the inert support with soluble compounds of the Group VIII metal and optional metal promoter, removing the solvent and drying the composition so obtained.

Before use in the second carbonylation reactor it is preferred to activate the catalyst, suitably by contacting the catalyst with a reducing gas at elevated temperature, preferably at a temperature in the range 150 to 600° C. The reducing gas may be selected from carbon monoxide, hydrogen, mixtures of carbon monoxide and hydrogen, or off-gas from a carbonylation process.

The second carbonylation reactor is suitably operated at elevated temperature and pressure. Suitably, the elevated temperature is in the range 150 to 350° C., for example about 200° C. Suitably, the elevated pressure is in the range 1 to 100 barg, preferably 20–30 barg. The second carbonylation reactor is suitably operated isothermally, with heat of reaction being removed by means known in the art, such as for example, an external steam drum with pressure control for generation of medium pressure steam.

The heterogeneous carbonylation process in the second carbonylation reactor may suitably be operated as a continuous process.

Preferably, the second carbonylation reactor is operated with down-flow so that any liquid products, unconsumed reactants and/or promoters may be removed easily from the reactor. The gases and/or vapours exiting the second carbonylation reactor may be passed through one or more condensers and/or coolers to condense liquid products, unconsumed reactants and/or promoters which may be separated from any residual gases and/or vapours and recycled to the first carbonylation reactor. Any residual gases and/or vapours may be disposed of by conventional means such as for example, by passing to conventional scrubbers and/or burners. If required, these are smaller than otherwise would be the case without the second carbonylation reactor of the present invention.

Condensation of liquid products within the second carbonylation reactor may reduce catalyst life, and is preferably avoided by control of reaction temperature. However, lower reaction temperature may be desirable in order to reduce reactor costs. The temperature at which condensation of product occurs in the second carbonylation reactor may be reduced by feeding excess alcohol and/or reactive derivative thereof so that the product is substantially an ester rather than the less volatile carboxylic acid. Alternatively, the temperature at which condensation occurs may be lowered by lowering the pressure or by recycling to the second carbonylation reactor some of the gaseous effluent from the downstream scrubbing system.

The process of the present invention will now be further illustrated by reference to the following Examples and by reference to the Figure which represents a flow scheme for the process of the present invention.

(I) Preparation of Catalysts

Heterogeneous catalysts suitable for use in the second carbonylation reactor in the process of the present invention were prepared and tested.

Catalyst A

Catalyst A comprising rhodium (0.48% w/v) supported on microporous AR2 (Trade Mark) carbon (ex Sutcliffe Speakman) was prepared as follows:

Microporous AR2 (Trade Mark) carbon (50 g) was washed free of metal impurities by adding the carbon to a solution of 20% v/v nitric acid (250 ml) and heating the solution at its boiling point for a period of 1 hour. The carbon was isolated from the nitric acid solution by filtration and was then washed with 4 litres of cold distilled water before being dried in an oven at a temperature of 115° C. for 3 hours.

A solution of 0.203 g of $RhCl_3$ in 40 ml of acetone was added to 20 ml of the washed and dried carbon. This is equivalent to 0.1 g of rhodium per 10 ml of carbon support (i.e. 0.48% w/v metal loading). The solvent was then removed by rotary evaporation at 40° C. for 1 hour and at 80° C. for a further hour. The resulting catalyst was dried in an oven at 110° C. overnight after which the catalyst was ready for use.

Catalyst B

Catalyst B comprising rhodium (0.48% w/v) supported on mesoporous carbon (grade Wv1100; ex Westvaco Corp.) was prepared as follows:

The mesoporous carbon (50 g) was washed free of metal impurities by adding the carbon in a solution of 20% v/v nitric acid (250 ml) and heating the solution at its boiling point for a period of 1 hour. The carbon was isolated from the nitric acid solution by filtration and was then washed with 4 litres of cold distilled water before being dried in an oven at a temperature of 115° C. for 3 hours.

A solution of 0.203 g of $RhCl_3$ in 40 ml of acetone was added to 20 ml of the washed and dried mesoporous carbon. This is equivalent to 0.1 g of rhodium per 10 ml of carbon support (i.e. 0.48% w/v metal loading). The solvent was then removed by rotary evaporation at 40° C. for 1 hour and at 80° C. for a further hour. The resulting catalyst was dried in an oven at 110° C. overnight after which the catalyst was ready for use.

(II) Catalyst Test Rig

A Catalyst Test Rig comprising a Hastelloy (trade mark) reactor tube of internal diameter 0.5 inch and of length 28 inches with a 4 mm OD axial thermowell was used in the following experiments. Liquid feed was supplied to the reactor via a pump capable of delivering liquids under pressure. A process stream was removed from the reactor and was passed to a 100 ml volume condenser, constructed from Hastelloy (trade mark), where liquid products were condensed and collected. A gaseous stream was removed from the condenser and passed through a gas water meter to measure its volume.

(III) Activation Procedure

The catalysts prepared above were activated before testing in a heterogeneous process to illustrate their use in the second carbonylation reactor of the process of the present invention.

A standard activation procedure was used whereby 10 ml of the catalyst was loaded into the Catalyst Test Rig reactor, followed by 89 g of inert glass beads which act as a mixer/pre-bed. The catalyst was treated at a temperature of 300° C. with nitrogen at a flow rate of 130 ml/min for 12 hours. The catalyst was then reduced at a temperature of 188° C. and a flow rate of 136 mm in with a gas composition prepared to simulate the composition which would be expected downstream of a condenser placed in the off-gas vented from the first carbonylation reactor in the process of the present invention. The composition of this off-gas composition is given in Table 1.

The catalyst activation procedure was deemed to be complete when the levels of carbon monoxide and hydrogen exiting from the reactor, as monitored by GC, were the same as in the simulated off-gas stream fed to the reactor.

TABLE 1

| GAS COMPOSITION USED IN CARBONYLATION EXPERIMENTS | |
|---|---|
| Component | % mol |
| Hydrogen | 10.2 |
| Nitrogen | 17.9 |
| Carbon Monoxide | 63.3 |
| Carbon Dioxide | 5.6 |
| Methyl Iodide | 2.8 |
| Methyl Acetate | 0.1 |
| Acetic Acid | 0.1 |
| Water | 0.2 |

(IV) Heterogeneous Carbonylation Experiments

The catalysts prepared above were tested in a heterogeneous carbonylation process using the conditions summarised in Table 2 below to illustrate the second carbonylation reactor of the process of the present invention. Following activation of the catalyst, as described above, simulated off-gas was fed to the catalyst at a flow rate of 149 ml/min via a mass flow controller and the pressure of off-gas flowing through the reactor was then increased to 27 barg. After stabilisation at 27 barg for 30 minutes, liquid reactants were pumped to the reactor at a flow rate of 10.4 ml/hr via a high pressure pump. The volume of gas flowing out of the reactor was measured using a flow meter. The reaction was allowed to continue for approximately 40–50 hours. Samples of both gaseous and liquid products exiting the reactor were taken at least every 12 hours and were analysed by gas chromatography. The total mass of liquid products collected in the condenser at the end of the experiment was determined.

The gaseous product data (volume and composition) and product liquid data (weight and composition) were used to derive parameters (defined below) which measure the performance of the catalysts in utilising the carbon monoxide in the off-gas.

"C-mol" relates to the number of moles of carbon atoms in the carbonylation product which are derived from the alcohol reactant and/or reactive derivative thereof. For example, in Equation 1, the methyl acetate carbonylation product contains twice as many carbon atoms derived from the methanol reactant as the acetic acid carbonylation product;

$$4\ CH_3OH + 3\ CO \rightarrow CH_3CO_2CH_3 + 2\ CH_3CO_2H + H_2O \qquad (1)$$

In this example the C-mol selectivity is 50 C-mol % to each product since 2 moles of acetic acid are produced per mole of methyl acetate.

(V) Definitions

CO conversion (mol %) =

$$\frac{(\text{moles CO in feed}) - (\text{moles CO exiting reactor})}{(\text{moles CO in feed})} \times 100$$

MeOH conversion (mol %) =

$$\frac{(\text{moles MeOH in feed}) - (\text{moles MeOH exiting reactor})}{(\text{moles MeOH in feed})} \times 100$$

Acetyls selectivity (C-mol %) =

$$\frac{\text{C-moles in (MeOAc + AcOH) derived from MeOH}}{\text{(C-moles in total products derived from MeOH)}} \times 100$$

(VI) Results

EXAMPLES A AND B

The total conversion of carbon monoxide (mol %) and conversion of methanol (mol %) together with selectivity and productivity data for Catalysts A (Example A) and B (Example B) are given in Tables 3–4 and 5–6 respectively.

A comparison of the results in Tables 3 and 5 shows that a catalyst comprising rhodium supported on a mesoporous carbon support produces less methane (an undesirable by-product) than a catalyst comprising rhodium supported on a microporous carbon support and is therefore superior under the particular conditions of the test.

TABLE 2

| REACTION CONDITIONS | |
|---|---|
| CO: MeOH in feed | 1:1 (molar) |
| MeOH: MeI in feed | 22:1 (molar) |
| Catalyst Bed Volume | 10 ml[a] |
| Feed Gas Flow | 149 ml/min |
| Feed Liquid Flow | 10.4 ml/hr |
| Reaction Time on Stream | 40–50 hours |

[a]Equivalent to 4.98 and 2.95 g of Catalyst A and B respectively.

TABLE 3

| CATALYST A | | | | |
|---|---|---|---|---|
| Time on Stream (hr)[a] | 15.17 | 23.35 | 39.27 | 46.97 |
| Total CO Conversion mol % | 61.14 | 63.93 | 64.97 | 67.61 |
| MeOH conversion mol % | 96.65 | 97.07 | 97.11 | 97.39 |
| Selectivity C-mol % (from methanol) | | | | |
| $CH_4$ | 3.94 | 2.45 | 1.89 | 4.51 |
| DME | 4.34 | 4.53 | 4.39 | 3.91 |
| MeOAc | 61.47 | 57.48 | 60.14 | 54.96 |
| AcOH | 30.24 | 35.54 | 33.59 | 36.98 |
| (Acetyls)[b] | 91.72 | 93.02 | 93.72 | 91.94 |
| Totals | 100.00 | 100.00 | 100.00 | 100.00 |
| Productivity (mol/l-cat/h) | | | | |
| $H_2O$ | 3.04 | 2.63 | 2.61 | 2.62 |
| $CH_4$ | 0.90 | 0.53 | 0.43 | 0.97 |
| DME | 0.49 | 0.48 | 0.49 | 0.46 |
| MeOAc | 7.01 | 6.15 | 6.78 | 6.45 |
| AcOH | 6.89 | 7.61 | 7.58 | 8.68 |
| (Acetyls)[b] | 13.90 | 13.77 | 14.36 | 15.13 |

[a]Bed temperature = 188° C., Off-gas pressure = 27 barg
[b]Acetyls = acetic acid and methyl acetate
DME = dimethyl ether; MeOAc = methyl acetate; AcOH acetic acid

TABLE 4

| CATALYST A | |
|---|---|
| Time on Stream (hr)[a] | 6.10 |
| CO Conversion mol % | 11.71 |
| MeOH conversion mol % | 25.92 |
| Selectivity C-mol % (from methanol) | |
| MeOAc | 86.48 |
| AcOH | 0.00 |

[a]Bed temperature = 188° C., Off-gas pressure = 21 barg MeOAc = methyl acetate; AcOH = acetic acid

TABLE 5

| CATALYST B | | | | |
|---|---|---|---|---|
| Time on Stream (hr)[a] | 5.88 | 17.72 | 27.88 | 38.63 |
| Total CO Conversion mol % | 16.90 | 46.94 | 59.46 | 60.73 |
| MeOH conversion mol % | 33.64 | 85.80 | 94.67 | 96.93 |
| Selectivity C-mol % (from methanol) | | | | |
| $CH_4$ | 1.37 | 0.42 | 0.08 | 0.07 |
| DME | 10.10 | 11.13 | 2.44 | 2.40 |
| MeOAc | 88.53 | 53.99 | 60.34 | 56.13 |
| AcOH | 0.00 | 34.47 | 37.14 | 41.40 |
| (Acetyls)[b] | 88.53 | 88.45 | 97.48 | 97.53 |
| Totals | 100.01 | 100.00 | 100.01 | 100.01 |
| Productivity (mol/l-cat/h) | | | | |
| $H_2O$ | 2.78 | 2.15 | 3.13 | 3.02 |
| $CH_4$ | 0.10 | 0.08 | 0.02 | 0.02 |
| DME | 0.38 | 1.03 | 0.26 | 0.27 |
| MeOAc | 3.34 | 4.98 | 6.51 | 6.20 |
| AcOH | 0.00 | 6.36 | 8.02 | 9.15 |
| (Acetyls)[b] | 3.34 | 11.34 | 14.53 | 15.36 |

[a]Bed temperature = 188° C., Off-gas pressure = 27 barg
[b]Acetyls = acetic acid and methyl acetate
DME = dimethyl ether; MeOAc = methyl acetate; AcOH = acetic acid

TABLE B

| CATALYST B | | | | |
|---|---|---|---|---|
| Time on Stream (hr)[a] | 10.00 | 23.75 | 30.97 | 42.63 |
| TOTAL CO Conversion mol % | 57.06 | 46.22 | 40.40 | 33.73 |
| MeOH conversion mol % | 95.35 | 84.02 | 73.95 | 68.21 |
| Selectivity C-mol % (from methanol) | | | | |
| MeOAc | 70.41 | 73.20 | 89.04 | 91.39 |
| AcOH | 21.16 | 16.82 | 8.99 | 6.19 |

[a]Bed temperature = 250° C., Off-gas pressure = 27 barg
MeOAc = methyl acetate; AcOH = acetic acid

EXAMPLE C

A catalyst (catalyst C) comprising 1% w/w Rh supported on microporous carbon (Sutcliffe Speakman Co. grade AR2) was prepared as described under (I). 10 ml of this catalyst (4.97 g) were loaded into the reactor as described under (III).

The catalyst was activated at 250° C. by heating in 130 ml/min flowing nitrogen for 3 h followed by 140 ml/min of simulated off-gas. The off-gas flow rate was then maintained at 140 ml/min and the pressure increased to 28 bar. The liquid feed (MeOH, MeI etc) was then delivered to the reactor at 10.4 ml/h. The feed composition (see Table 7) in this example was designed to simulate the feedstream that would be obtained following the mixing of fresh methanol with typical methanol carbonylation plant off-gas recovered after passing through a condenser (dry, low-MeI type off-gas):

TABLE 7

| | Low-MeI off-gas | | | | | | | | | |
|---|---|---|---|---|---|---|---|---|---|---|
| Feed | CO | CO2 | H2 | N2 | MeOH | MeI | MeOAc | AcOH | H2O | Totals |
| % mol | 38.02 | 3.36 | 5.79 | 10.71 | 40.06 | 1.81 | 0.06 | 0.06 | 0.13 | 100 |

The CO:MeOH ratio of the feed was 0.95, and the contact time of the feed on the catalyst was 2.7 s. The carbonylation reaction between CO in the off-gas and MeOH was allowed to proceed for 29 h, with gas and liquid products analysed periodically. The data obtained is shown in Table 8.

TABLE 8

| | CATALYST C | | | |
|---|---|---|---|---|
| Time/h | 9.75 | 15.58 | 21.92 | 29.12 |
| Selectivity C-mol % | | | | |
| CH4 | 0.69 | 10.40 | 9.08 | 9.66 |
| DME | 0.00 | 2.44 | 2.39 | 1.94 |
| MeOAc | 5.80 | 5.32 | 5.41 | 0.00 |
| AcOH | 93.51 | 81.83 | 83.12 | 88.41 |
| (Acetyls) | 99.31 | 87.16 | 88.53 | 88.41 |
| Totals | 100.0 | 100.0 | 100.0 | 100.0 |
| Conversion % | | | | |
| CO | 92.59 | 76.52 | 78.85 | 80.65 |
| MeOH | 97.12 | 97.35 | 97.24 | 100.00 |

The data in Table 8 indicates that the Rh/carbon catalyst is capable of scrubbing CO from simulated off-gas of composition 'dry, low-MeI' with a high efficiency of 70%+, despite the low level of MeI of 3 mol % available as a promoter. Moreover, selectivity to by-product methane is <10% C-mol, despite the high catalyst bed temperature of 260° C. observed in this test.

Example D

A catalyst (catalyst D) comprising 1% w/w Rh supported on microporous carbon (Sutcliffe Speakman Co. grade AR2) was prepared as described under (I). 2 ml of this catalyst (0.96 g) were loaded in the reactor as described under (II).

The catalyst was activated by heating at 188° C. in flowing nitrogen at 130 ml/min for 3 h then in 100 ml/min of simulated off-gas for 3 h. The off-gas flow rate was then reduced to 24 ml/min and the pressure increased to 28 bar. The liquid feed (MeOH, MeI etc) was then delivered to the reactor at 5.6 ml/h. The feed composition (See Table 9) in this example was designed to simulate the feedstream that would be obtained following the mixing of fresh methanol with typical methanol carbonylation plant off-gas recovered before passing through a condensor (wet, high MeI type off-gas):

TABLE 9

| | Low-MeI off-gas | | | | | | | | | |
|---|---|---|---|---|---|---|---|---|---|---|
| Feed | CO | CO2 | H2 | N2 | MeOH | MeI | MeOAc | AcOH | H2O | Totals |
| % mol | 24.16 | 1.8 | 3.58 | 2.47 | 24.05 | 16.47 | 0.82 | 12.69 | 13.69 | 100 |

The CO:MeOH ratio of the feed was 1.0, and the contact time of the feed on the catalyst was 1.7 s. The carbonylation reaction between CO in the off-gas and MeOH was allowed to proceed for 29 h, with gas and liquid products analysed periodically. The data obtained is shown in Table 10.

TABLE 10

| | CATALYST D | |
|---|---|---|
| Time/h | 5.33 | 29.20 |
| Bed temp (° C.) | 197 | 196 |
| Selectivity C-mol % | | |
| CH4 | 0.03 | 1.19 |
| DME | 1.63 | 0.69 |
| MeOAc | 13.24 | 15.36 |
| AcOH | 85.09 | 82.76 |
| (Acetyls) | 98.33 | 98.12 |
| Totals | 100.00 | 100.00 |
| Conversion % | | |
| CO | 92.78 | 91.47 |
| MeOH | 93.23 | 92.14 |

The data in Table 10 indicates that the catalyst is capable of scrubbing CO at efficiencies of 90%+ from wet, high-MeI off-gas, despite the conditions of lower temperature (bed temperature 197° C.) and higher throughput (1.7 s contact time) than were used in Example 1. The high efficiency observed is probably due to the high level of MeI promoter (16.47 mol %) available in the feed. By-product methane selectivity was very low at <2% C-mol, indicative both of the predominance of the carbonylation reaction and of the low catalyst bed temperature of 197° C. observed in the test.

Examples (A) to (D) are not examples according to the present invention because they are only illustrative of feature (c) of the process of the invention.

Carbonylation Apparatus

FIG. 1 illustrates a carbonylation apparatus for use in the process of the present invention which apparatus comprises a first carbonylation reactor (1), an off-gas vent line (6), a methanol feed line (7), a second carbonylation reactor (2), a cooler (3), a reactor vent condenser (4), a reactor vent condenser separator (5), a recycle line (8), and a high pressure absorber (9).

In use, an off-gas stream (10) is withdrawn from the first carbonylation reactor (1) and is passed along the off-gas vent line (6) where the off-gas stream is mixed with methanol from the methanol feed line (7). Alternatively, the off-gas is passed through a condenser and separator (not shown) to remove a portion of the condensable material before being mixed with methanol from the feed line (7). A methanol injector may be required to minimise thermal shock in the off-gas vent line (6). Alternatively, the methanol feed may be vaporised and heated prior to mixing with the off-gas stream (6) or admission to the second carbonylation reactor (2).

The resulting mixed stream of off-gas and methanol (11) is then fed to the head of a second carbonylation reactor (2). The second carbonylation reactor (2) is multitubular and is operated isothermally with the mixed stream (11) flowing downwardly through the reactor (2). A first section of tubes is required to heat the mixed stream (11) to reaction temperature. Heat of reaction is removed from the second carbonylation reactor (2) by way of medium pressure steam via cooler (3) which comprises an external steel drum with pressure control.

A product stream (12) is removed from the second carbonylation reactor (2) and is passed to a reactor vent condenser (4) in which the product stream (12) is cooled to a temperature at which most of the acetic acid carbonylation product and methyl iodide promoter condenses. The stream (13) which exits the reactor vent condenser (4) is passed to a reactor vent condenser separator (5) where the condensed products (14) are separated and returned via recycle line (8) to the first carbonylation reactor (1). The non-condensed process stream (15) is passed to the high pressure absorber (9).

EXAMPLE

The process of the present invention using the apparatus described above, was simulated using an ASPEN (Trade Mark) computer model. In the simulation, the off-gas stream (10) is withdrawn from the first carbonylation reactor (1) at a temperature of approximately 188° C. and at a pressure of 28.6 bara. Methanol is fed along line (7) at a temperature of 20° C. Addition of the cooler methanol stream to the off-gas stream results in at least some of the condensable products from the first carbonylation reactor (1) condensing. The amount of methanol added to the off-gas stream is such as to maintain a 1.5:1 molar ratio of carbon monoxide to methanol in the mixed stream (11) feed to the second carbonylation reactor (2). The mixed stream (11) is at a temperature of approximately 177° C. while the second carbonylation reactor (2) is operated isothermally at a temperature of 200° C. The reaction exotherm of 1.28 MW will be expected to be sufficient to raise 2.4 te/hr of steam at 15.6 bara in the cooler (3).

Owing to the presence of condensed reactor products and the high reaction temperature Hastelloy will probably not be an acceptable material of construction for the second carbonylation reactor (2) and therefore zirconium is expected to be required to be used.

In the computer simulation it is assumed that 100% conversion of methanol and 100% selectivity to acetic acid is achieved.

In the computer model the product stream (12) from the second carbonylation reactor (2) is cooled to a temperature of 60° C. in the reactor vent condenser (4) and passed to a separator (5) from which a liquid stream comprising carbonylation products from the second carbonylation reactor is withdrawn and recycled to the first carbonylation reactor via line (8). The non-condensable gases comprising carbon monoxide is passed to conventional high pressure adsorber (9).

A summary mass balance for the computer simulation is given in Table 7 below.

Using the process of the present invention, less carbon monoxide will be passed to the high pressure adsorber than would be the case without the second carbonylation reactor. Therefore, the overall yield of carbonylation products based upon carbon monoxide is increased.

TABLE 7

| STREAM SECTION | | | | | |
|---|---|---|---|---|---|
| STREAM ID | 11 | 12 | 13 | 10 | 15 |
| SUBSTREAM: MIXED PHASE: COMPONENTS: KMOL/HR | MIXED | MIXED | MIXED | VAPOR | VAPOR |
| H2 | 8.0800 | 8.0800 | 8.0800 | 8.0800 | 7.5243 |
| CH4 | 0.0 | 0.0 | 0.0 | 0.0 | 0.0 |
| N2 | 5.5900 | 5.5900 | 5.5900 | 5.5900 | 5.1257 |
| CO | 54.5500 | 18.1400 | 18.1400 | 54.5500 | 16.4402 |
| CO2 | 4.0700 | 4.0700 | 4.0700 | 4.0700 | 2.1424 |
| CH3OH | 36.4100 | 0.0 | 0.0 | 3.0000 − 02 | 0.0 |
| CH3I | 37.1000 | 37.1000 | 37.1000 | 37.1000 | 2.1473 |
| CH3COOCH | 1.8600 | 1.8600 | 1.8600 | 1.8600 | 3.1008 − 02 |
| CH3COOH | 28.7900 | 65.2000 | 65.2000 | 28.7900 | 8.5741 − 02 |
| H2O | 31.6400 | 31.6400 | 31.6400 | 31.6400 | 0.1490 |
| HI | 3.0000 − 02 | 3.0000 − 02 | 3.0000 − 02 | 3.0000 − 02 | 5.2256 − 08 |
| C2H5COOH | 3.0000 − 02 | 3.0000 − 02 | 3.0000 − 02 | 3.0000 − 02 | 1.6103.05 |
| RH | 0.0 | 0.0 | 0.0 | 0.0 | 0.0 |
| TOTAL FLOW: | | | | | |
| KMOL/HR | 208.1500 | 171.7400 | 171.7400 | 171.7700 | 33.6458 |
| KG/HR | 1.0755 + 04 | 1.0755 + 04 | 1.0755 + 04 | 9589.6350 | 1028.4671 |
| CUM/SEC | 5.3654 − 02 | 4.2209 − 02 | 1.0865 − 02 | 5.9160 − 02 | 8.9125 − 03 |
| STATE VARIABLES: | | | | | |
| TEMP C. | 167.1236 | 200.0000 | 60.0000 | 188.8000 | 60.0073 |
| PRES BAR | 28.6000 | 28.6000 | 28.6000 | 28.6000 | 28.6000 |

TABLE 7-continued

| STREAM SECTION | | | | | |
|---|---|---|---|---|---|
| VFRAC | 0.7641 | 0.6990 | 0.1959 | 1.0000 | 1.0000 |
| LFRAC | 0.2358 | 0.3009 | 0.8040 | 0.0 | 0.0 |
| SFRAC | 0.0 | 0.0 | 0.0 | 0.0 | 0.0 |
| ENTHALPY: | | | | | |
| J/KMOL | −1.7300 + 08 | −2.3558 + 08 | −2.6153 + 08 | −1.5885 + 08 | −7.9934.07 |
| J/KG | −3.3480 + 06 | −3.7617 + 06 | −4.1762 + 06 | −2.8454 + 06 | −2.6150 + 06 |
| WATT | −1.0003 + 07 | −1.1239 + 07 | −1.2477 + 07 | −7.5795 + 06 | −7.4707 + 05 |
| ENTROPY: | | | | | |
| J/KMOL-K | −5.1780 + 04 | −9.2849 + 04 | −1.5506 + 05 | −1.6894 + 04 | 2.8826 + 04 |
| J/KG-K | −1002.1077 | −1482.5967 | −2476.0569 | −302.5992 | 943.0387 |
| DENSITY: | | | | | |
| KMOL/CUM | 1.0776 | 1.1302 | 4.3909 | 0.8065 | 1.0486 |
| KG/CUM | 55.6830 | 70.7814 | 274.9853 | 45.0270 | 32.0542 |
| AVG MW | 51.6710 | 62.6256 | 62.6256 | 55.8283 | 30.5673 |

| STREAM ID | 14 | 16 | 17 | 18 | METHANOL |
|---|---|---|---|---|---|
| SUBSTREAM: MIXED PHASE | LIQUID | LIQUID | VAPOR | LIQUID | LIQUID |
| COMPONENTS: KMOL/HR | | | | | |
| H2 | 0.5557 | 0.0 | 7.4736 | 5.0670 − 02 | 0.0 |
| CH4 | 0.0 | 0.0 | 0.0 | 0.0 | 0.0 |
| N2 | 0.4642 | 0.0 | 5.0592 | 6.6524 − 02 | 0.0 |
| CO | 1.6997 | 0.0 | 16.2365 | 0.2037 | 0.0 |
| CO2 | 1.9275 | 0.0 | 1.8514 | 0.2910 | 0.0 |
| CH3OH | 0.0 | 1.0000 − 02 | 1.1926 − 04 | 9.8807 − 03 | 36.3800 |
| CH3I | 34.9526 | 0.0 | 2.7164 − 04 | 2.1470 | 0.0 |
| CH3COOCH | 1.8289 | 0.1900 | 6.3904 − 03 | 0.2146 | 0.0 |
| CH3COOH | 65.1142 | 21.6500 | 6.2690 − 02 | 21.6730 | 0.0 |
| H2O | 31.4909 | 0.4800 | 3.0085 − 03 | 0.6260 | 0.0 |
| HI | −3.0000 − 02 | 0.0 | 0.0 | 5.2256 − 08 | 0.0 |
| C2H5COOH | 2.9984 − 02 | 1.0000 − 02 | 1.3042 − 05 | 1.0003 − 02 | 0.0 |
| RH | 0.0 | 0.0 | 0.0 | 0.0 | 0.0 |
| TOTAL FLOW: | | | | | |
| KMOL/HR | 138.0941 | 22.3400 | 30.6933 | 25.2925 | 36.3800 |
| KG/HR | 9726.8631 | 1323.9224 | 697.4007 | 1654.9888 | 1165.6952 |
| CUM/SEC | 1.9520 − 03 | 3.4847 − 04 | 7.5724 − 03 | 4.1379 − 04 | 3.9978 − 04 |
| STATE VARIABLES: | | | | | |
| TEMP C. | 60.0073 | 28.6000 | 32.0625 | 67.7331 | 20.0000 |
| PRES BAR | 28.6000 | 28.6000 | 28.4600 | 28.5300 | 28.6000 |
| VFRAC | 0.0 | 0.0 | 1.0000 | 0.0 | 0.0 |
| LFRAC | 1.0000 | 1.0000 | 0.0 | 1.0000 | 1.0000 |
| SFRAC | 0.0 | 0.0 | 0.0 | 0.0 | 0.0 |
| ENTHALPY: | | | | | |
| JIKMOL | −3.0578 + 08 | −4.7709 + 08 | −8.3192 + 07 | −4.2677 + 08 | −2.3977 + 08 |
| J/KG | −4.3412 + 06 | −8.0505 + 06 | −3.6614 + 06 | −6.5222 + 06 | −7.4830 + 06 |
| WATT | −1.1730 + 07 | −2.9606 + 06 | −7.0929 + 05 | −2.9984 + 06 | −2.4230 + 06 |
| ENTROPY: | | | | | |
| J/KMOL-K | −1.9987 + 05 | −3.1037 + 05 | 2.8982 + 04 | −2.6980 + 05 | −2.4510 + 05 |
| J/KG-K | −2837.5382 | −5237.2822 | 1275.5401 | −4123.3265 | −7649.1979 |
| DENSITY: | | | | | |
| KMOL/CUM | 19.6516 | 17.8079 | 1.1259 | 16.9788 | 25.2776 |
| KG/CUM | 1384.1956 | 1055.3397 | 25.5825 | 1110.9875 | 809.9525 |
| AVG MW | 70.4364 | 59.2624 | 22.7215 | 65.4337 | 32.0422 |

I claim:

1. A carbonylation process which comprises (a) contacting, in a first carbonylation reactor at elevated temperature and pressure, an alcohol having n carbon atoms and/or a reactive derivative thereof with carbon monoxide in a liquid reaction composition comprising a halogen and/or halogen compound promoter and a Group VIII noble metal carbonylation catalyst to produce a carbonylation product comprising a carboxylic acid having n+1 carbon atoms and/or an ester of the carboxylic acid having n+1 carbon atoms and the alcohol having n carbon atoms and/or an anhydride of the carboxylic acid having n+1 carbon atoms; (b) withdrawing from the first carbonylation reactor, an off-gas stream comprising carbon monoxide and optionally halogen and/or halogen compound promoter, and optionally carbonylation product; and (c) contacting in a second carbonylation reactor, the withdrawn off-gas stream with an alcohol having m carbon atoms and/or a reactive derivative thereof in the presence of a halogen and/or halogen compound promoter and a heterogeneous carbonylation catalyst comprising a supported Group VIII noble metal to produce a further carbonylation product comprising a carboxylic acid having m+1 carbon atoms and/or an ester of the carboxylic acid having m+1 carbon atoms and the alcohol having m carbon atoms and/or an anhydride of the carboxylic acid having m+1 carbon atoms.

2. A process according to claim 1 wherein in the first carbonylation reactor methanol or a reactive derivative thereof is contacted with carbon monoxide.

3. A process according to either claim 1 or claim 2 wherein in the second carbonylation reactor methanol or a reactive derivative thereof is contacted with the off-gas stream withdrawn from the first carbonylation reactor.

4. A process according to claim 1 wherein the reactive derivative of the alcohol having n carbon atoms or the alcohol having m carbon atoms is methyl acetate, dimethyl ether or methyl iodide.

5. A process according to claim 1 wherein the halogen and/or halogen compound promoter used in the first and second carbonylation reactors is an alkyl iodide.

6. A process according to claim 5 wherein the alkyl iodide is methyl iodide.

7. A process according to claim 1 wherein the Group VIII noble metal carbonylation catalyst in the first carbonylation reactor is an iridium or rhodium-containing compound which is soluble in the liquid reaction composition.

8. A process according to claim 7 wherein the Group VIII noble metal carbonylation catalyst is iridium and the liquid reaction composition contains a co-promoter selected from the group consisting of ruthenium, osmium, rhenium, cadmium, mercury, zinc, indium and gallium.

9. A process according to claim 7 wherein the Group VIII noble metal carbonylation catalyst is rhodium and the liquid reaction composition contains a co-promoter selected from alkali metals and/or an organic iodide.

10. A process according to claim 1 wherein in the first carbonylation reactor water is present in the liquid reaction composition in a concentration in the range 0.1 to 15% by weight and carboxylic acid is produced by the process.

11. A process according to claim 1 wherein in the first carbonylation reactor the liquid reaction composition is substantially anhydrous and carboxylic acid anhydride is produced by the process.

12. A process according to claim 1 wherein the off-gas withdrawn from the first carbonylation reactor additionally comprises volatile halogen and/or halogen compound promoter.

13. A process according to claim 12 wherein the promoter in the off-gas withdrawn from the first carbonylation reactor is sufficient for the requirements of the second carbonylation reactor.

14. A process according to claim I wherein the second carbonylation reactor is a multi-tubed heterogeneous reactor packed with a heterogeneous carbonylation catalyst.

15. A process according to claim 1 wherein the heterogeneous carbonylation catalyst in the second carbonylation reactor comprises a Group VIII metal selected from the group consisting of iridium, rhodium and nickel, and an optional metal promoter, on an inert support.

16. A process according to claim 15 wherein the inert support is carbon.

17. A process according to claim 1 wherein in the second carbonylation reactor the heterogeneous carbonylation catalyst comprises rhodium, and optionally ruthenium, supported on a carbon support.

18. A process according to claim 1 wherein in the second carbonylation reactor the heterogeneous catalyst comprises iridium, and optionally ruthenium, supported on a carbon support.

19. A process according to claim 2 wherein in the first carbonylation reactor the liquid reaction composition is substantially anhydrous and carboxylic acid anhydride is produced by the process.

20. A process according to claim 3 wherein in the first carbonylation reactor the liquid reaction composition is substantially anhydrous and carboxylic acid anhydride is produced by the process.

21. A process according to claim 4 wherein in the first carbonylation reactor the liquid reaction composition is substantially anhydrous and carboxylic acid anhydride is produced by the process.

22. A process according to claim 5 wherein in the first carbonylation reactor the liquid reaction composition is substantially anhydrous and carboxylic acid anhydride is produced by the process.

23. A process according to claim 6 wherein in the first carbonylation reactor the liquid reaction composition is substantially anhydrous and carboxylic acid anhydride is produced by the process.

24. A process according to claim 7 wherein in the first carbonylation reactor the liquid reaction composition is substantially anhydrous and carboxylic acid anhydride is produced by the process.

25. A process according to claim 8 wherein in the first carbonylation reactor the liquid reaction composition is substantially anhydrous and carboxylic acid anhydride is produced by the process.

26. A process according to claim 9 wherein in the first carbonylation reactor the liquid reaction composition is substantially anhydrous and carboxylic acid anhydride is produced by the process.

* * * * *